(12) United States Patent
Wiesen et al.

(10) Patent No.: US 11,571,503 B2
(45) Date of Patent: Feb. 7, 2023

(54) METHOD AND APPARATUS FOR ADDING AN ANTICOAGULANT TO THE BLOOD OF A PATIENT

(71) Applicant: Fresenius Medical Care Deutschland GmbH, Bad Homburg (DE)

(72) Inventors: Gerhard Wiesen, Bad Homburg (DE); Reiner Spickermann, Burghausen (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 369 days.

(21) Appl. No.: 16/622,331

(22) PCT Filed: Jun. 14, 2018

(86) PCT No.: PCT/EP2018/065891
§ 371 (c)(1),
(2) Date: Dec. 13, 2019

(87) PCT Pub. No.: WO2018/229229
PCT Pub. Date: Dec. 20, 2018

(65) Prior Publication Data
US 2020/0197597 A1 Jun. 25, 2020

(30) Foreign Application Priority Data
Jun. 14, 2017 (DE) .................... 10 2017 113 061.6

(51) Int. Cl.
*A61M 1/36* (2006.01)
*A61K 31/727* (2006.01)
*A61M 1/26* (2006.01)

(52) U.S. Cl.
CPC ......... *A61M 1/3672* (2013.01); *A61K 31/727* (2013.01); *A61M 1/267* (2014.02); *A61M 2202/0478* (2013.01); *A61M 2205/3389* (2013.01); *A61M 2205/50* (2013.01); *A61M 2205/52* (2013.01); *A61M 2230/04* (2013.01)

(58) Field of Classification Search
CPC .............. A61M 1/3672; A61M 1/267; A61M 2202/0478; A61M 2205/3389; A61M 2205/50; A61M 2205/52; A61M 2230/04; A61K 31/727
See application file for complete search history.

(56) References Cited

U.S. PATENT DOCUMENTS 3,985,123 A * 10/1976 Herzlinger ............. A61B 5/411
600/526
5,656,027 A * 8/1997 Ellingboe ........... A61M 1/3672
604/541

(Continued)

FOREIGN PATENT DOCUMENTS

WO  WO 2016/168162  10/2016

*Primary Examiner* — Tatyana Zalukaeva
*Assistant Examiner* — Rachel O'Connell
(74) *Attorney, Agent, or Firm* — Jacobson Holman PLLC

(57) ABSTRACT

The present invention relates to a method of adding an anticoagulant to the blood of a patient, wherein the addition takes place in the form of a bolus, wherein the bolus application time B depends on the values TBV and CO, with TBV representing the blood volume of the patient and CO the cardiac output of the patient. The present invention furthermore relates to an apparatus for adding a coagulant to the blood of a patient.

14 Claims, 2 Drawing Sheets

(56) References Cited

U.S. PATENT DOCUMENTS

Figure 1:
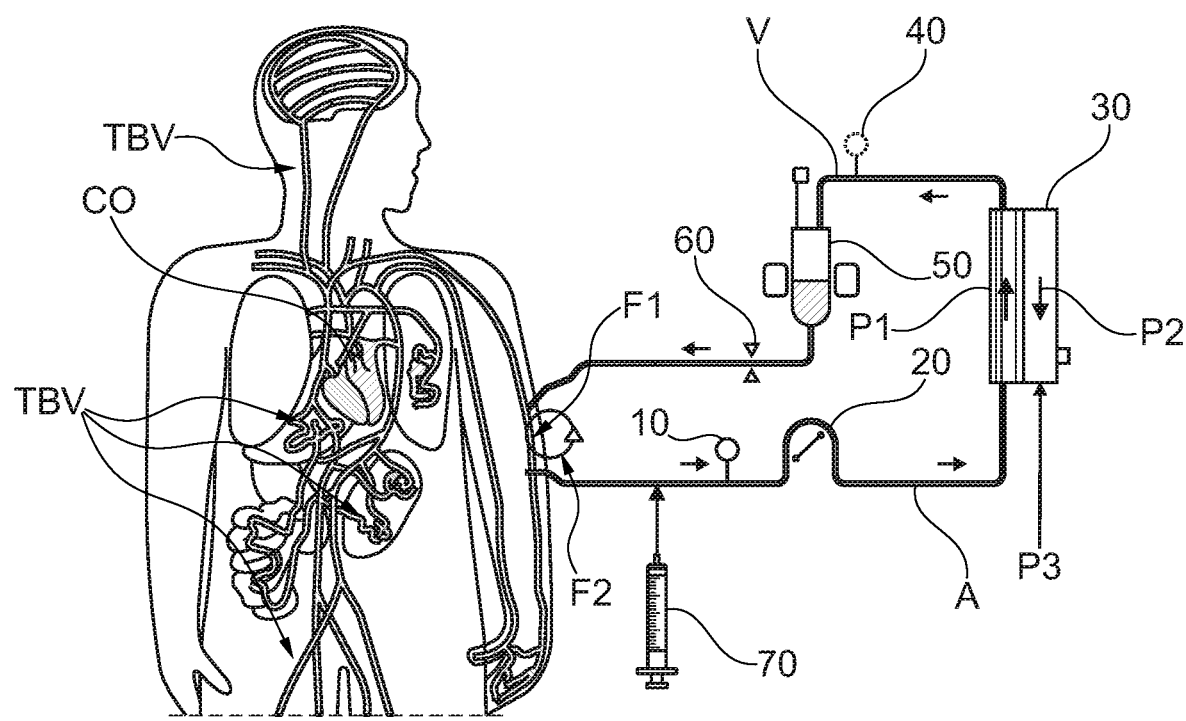

| | | | |
|---|---|---|---|
| 6,017,318 A | 1/2000 | Gauthier et al. | |
| 2007/0066928 A1* | 3/2007 | Lannoy | A61M 1/3609 604/6.07 |
| 2008/0015434 A1* | 1/2008 | Rubinstein | A61B 5/0275 600/431 |
| 2013/0020237 A1* | 1/2013 | Wilt | A61M 1/3603 210/85 |
| 2017/0000938 A1 | 1/2017 | Wilt et al. | |

\* cited by examiner

METHOD AND APPARATUS FOR ADDING AN ANTICOAGULANT TO THE BLOOD OF A PATIENT

The present invention relates to a method and to an apparatus for adding a coagulant to the blood of a patient.

During a dialysis treatment, the blood of the patient to be treated is withdrawn from the patient by means of an extracorporeal blood circuit, is conducted through a dialyzer, and is led back to the patient after the blood treatment has taken place therein. The conducting of the blood through the extracorporeal circuit is repeated multiple times to achieve the desired treatment objective.

In addition to the intimal injury by the dialysis cannulae by means of which the blood is withdrawn from the vascular system of the patient and is returned to it again, the blood comes into contact with different materials and large surfaces—typically between 1 m² and 2 m²—on flowing through the extracorporeal circuit. The flow guidance in the extracorporeal circuit is furthermore not ideal due to the T pieces, the invasive blood pressure measurement over a transducer protector, etc., for example, in the sense that dead zones, edges, other flow obstacles, and positions with direct blood-to-air contact are present.

All these interference positions can have the result that the blood coagulation is activated, which has the consequence that the treatment has to be aborted because a blood clot, for example, blocks the venous clot catcher that is intended to prevent the entry of clots into the blood circuit of the patient so that blood clots in the capillaries of the dialyzer, etc.

To avoid blood clotting and the disadvantages associated therewith, it is known from the prior art to add a coagulant that is preferably heparin to the blood.

Two types of heparin are distinguished, the unfractionated standard heparin having molecule sizes between 6,000 Da and 30,000 Da and the fractionated low molecular weight heparin (LMW heparin) having molecule sizes between 4,000 Da and 6,000 Da. In an aqueous solution, so-called high-flux dialyzer membranes allow fractionated heparin, i.e. LMW heparin having a screen coefficient of almost 1, to pass, which corresponds to an almost 100% elimination of the heparin over the membrane. Standard heparin passes the dialyzer membrane with a slightly reduced probability.

In contrast to this, heparin (LMW heparin or standard heparin) that is bound to proteins is not dialyzable, i.e. it is not transported over the dialyzer membrane into the dialysis liquid either by means of convection or by means of diffusion.

There is the problem at the start of the extracorporeal blood treatment that an increased initial heparin loss can occur. This is due to the fact that the extracorporeal blood circuit is filled with a so-called priming solution, i.e. with a physiological saline solution or with a dialysis solution, at the start of the blood treatment. As the intermixing with blood starts, the protein concentration and thus the heparin binding capacity is correspondingly reduced.

In addition, there is the fact that the dialyzer membrane is not yet covered by a secondary membrane of proteins (whose formation takes approximately 20-30 min.).

Both have the consequence that the heparin addition to the extracorporeal blood circuit at an early point in time has the result that a large part of the added heparin passes over the dialyzer membrane and is transported away with the dialysis liquid that flows over the dialyzer membrane on the other membrane side. This heparin is then no longer available for the anticoagulation of the blood.

It is the underlying object of the present invention to provide a method and an apparatus with which it is ensured that sufficient anticoagulant supply of the blood is present.

This object is achieved by a method having the features of claim 1 and by an apparatus having the features of claim 10.

Provision is accordingly made that the bolus application time B depends on the values TBV and CO, where TBV represents the blood volume of the patient and CO represents the cardiac output per minute of the patient.

Provision is preferably made that the bolus application time, i.e. the time duration in which the anticoagulant is added, is equal to or larger than the value T=TBV/CO.

It is achieved by the determination of the bolus application time in dependence on the parameter T or on TBV and CO that the anticoagulant is added at a rate that is adapted to the internal blood replacement rate.

This does not allow the anticoagulant to be supplied either too fast, which brings about the above-described disadvantage that some of the anticoagulant is removed via the dialyzer membrane, or too slowly, which brings about the disadvantage that the blood may possibly tend to anticoagulation since the anticoagulation concentration is too low.

The anticoagulant is applied at the rate $Q_{hep}=V_{hep}/B$, where $Q_{hep}$ is the volume rate to be applied in volume/time unit of the anticoagulant and $V_{hep}$ is the volume of the anticoagulant to be applied.

The anticoagulant is preferably heparin, but the invention is not restricted to this anticoagulant.

It is conceivable that the addition of the anticoagulant takes place by means of a pump, preferably by means of a standard heparin pump.

Provision is furthermore preferably made that the addition of the anticoagulant takes place into the extracorporeal circuit of a blood treatment device, in particular a dialysis machine.

The bolus addition preferably takes place in the form of a rectangular profile at a constant conveying rate of the pump.

The term of adding "to the blood of the patient" used as part of the invention thus includes both the case that the anticoagulant is injected directly into the blood circuit of the patient and the case that the anticoagulant is introduced into the extracorporeal circuit that is, for example, filled with a priming solution.

Provision is made in a further preferred embodiment of the invention that the addition of the anticoagulant is carried out prior to the blood treatment of the patient, in particular prior to the dialysis treatment of the patient.

The value TBV and/or the value CO can be determined prior to the anticoagulant addition by a method familiar to the skilled person, which is comparatively complex and/or expensive, or it can be read out of a memory in which these values are stored in an individual patient manner.

It is achieved by the procedure in accordance with the invention that the anticoagulant is distributed rapidly and evenly over the total blood volume of the patient. Too fast an addition of anticoagulant that would result in the above-described effect that there is not sufficient time for the binding of the anticoagulant to the proteins of the blood is prevented by the present invention so that the anticoagulant passes over the membrane of the dialyzer in the non-bound state and is thus no longer available for the anticoagulation effect.

It is the underlying idea of the present invention to dimension the duration of the addition of the anticoagulant so that blood freshly provided with an anticoagulant is metered into the blood circuit of the patient in an ideal ratio.

The infusion rate of the anticoagulant is adapted to the blood volume and to the cardiac output (CO), i.e. to the cardiac output per minute, of the patient and thus to his individual inner blood replacement rate. The cardiac output or also the cardiac output over time is the volume of blood that is conveyed by the heart of the patient per time unit. It is usually given in the unit l/min.

The cardiac output is inter alia dependent on the heart rate and in adults is typically in the range from 4.5-5 l/min. at rest.

Both the cardiac output and the blood volume of the patient can be determined by means of methods familiar to the skilled person.

Examples include echocardiography or the indirect calculation such as by means of the arterial stiffness monitor, dilution methods (boli), blood volume monitor (BVM), blood temperature monitor (BTM), thermodilution, etc.

Since the determination of the CO is time-intensive, it is also conceivable to store the patient-specific CO value as the "CO value at rest" in a memory. This can take place, for example, in the memory of the dialysis machine or of another treatment device, in a patient file, on a patient card, etc.

The present invention furthermore relates to an apparatus for adding an anticoagulant to the blood of a patient, wherein the addition takes place in the form of a bolus, wherein the apparatus has means for determining the bolus application time B in dependence on the values TBV and CO, where TBV represents the blood volume of the patient and CO represents the cardiac output of the patient, and wherein the apparatus furthermore has means for administering the anticoagulant within the specific bolus application time.

Provision is preferably made that the means for determining the bolus application time are designed such that the relationship B T is satisfied, that is that the bolus application time corresponds to or exceeds the value T.

The apparatus can have means for determining TBV and/or CO.

Alternatively or additionally, a memory can be provided which the apparatus has access to or which forms a component of the apparatus and in which the values for TBV and/or CO are stored so that T can be calculated in an individual patient manner from the stored values.

The means for administering the anticoagulant are, for example, designed as a pump, with the pump preferably being arranged such that it conveys the anticoagulant into the extracorporeal blood circuit of a blood treatment device.

As stated above, the anticoagulant is preferably heparin, but other anticoagulants can also be used.

The apparatus in accordance with the invention can be a component of a blood treatment device, preferably of a dialysis machine, or can be connected in a suitable manner to a blood treatment device, preferably to a dialysis machine.

Provision is preferably made that the skilled person also takes account of the blood distribution in the body of the patient, of the dead times, lead times, and follow-up times of the anticoagulant pump, of the clearance of the anticoagulant, of the technical data of the filter or of the dialyzer, and of the diffusive and convective transport mechanisms over the filter/dialyzer in the administration of the bolus of the anticoagulant or in the bolus application time.

The administered heparin can, for example, be unfractionated, high-molecular weight heparin or LMW heparin.

The present invention furthermore relates to a blood treatment device, in particular to a blood treatment device having an extracorporeal blood circuit, and particularly preferably a dialysis machine.

Further details and advantages of the invention will be explained in more detail with reference to an embodiment shown in the drawing.

There are shown:

FIG. 1: a schematic view of a patient connected to a dialysis machine; and

Figure 2:
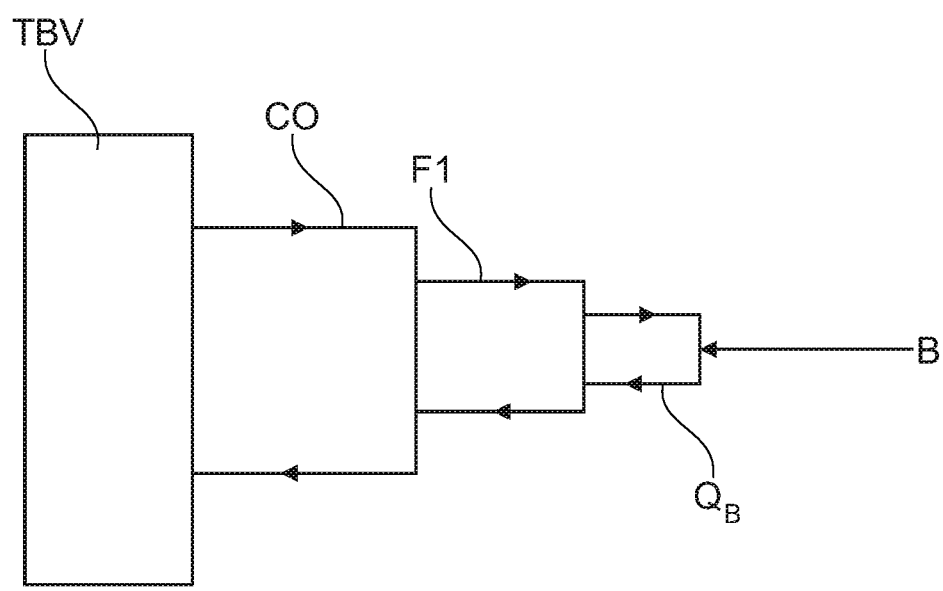

FIG. 2: a schematic representation of the flows of the arrangement in accordance with FIG. 1.

As can be seen from FIG. 1, the patient is connected to an extracorporeal blood circuit of a dialysis machine by means of a fistula and the arterial branch of said dialysis machine is marked by the reference symbol A and its venous branch by the reference symbol V. The direction of flow of the blood through the extracorporeal circuit is indicated by arrows.

The blood moves through the arterial branch A in which the pressure measurement device 10 and the blood pump 20 are located to the dialyzer 30 and from there into the venous branch V. The venous pressure measurement device 40 and the venous drip chamber 50 are located therein. The venous clamp 60 is arranged downstream of the drip chamber 50. The blood moves back to the patient after passing this clamp.

The blood flow in the dialyzer 30 is marked by the arrow P1 and the dialyzate flow by the arrow P2. The blood and the dialyzate are separated from one another by one or more semipermeable membranes, preferably by a hollow fiber bundle. As can be seen from the arrows P1 and P2, the dialyzer 30 in the embodiment shown is flown through by blood and dialyzate in counter current flow.

The arrow P3 designates the risk of heparin loss over the membrane of the dialyzer that is in particular present when the heparin has not yet bonded to the proteins of the blood, for instance because it was added at too great a speed or within too short a time.

Reference symbol F1 marks the fistula flow and the circle in the region of the fistula marks a possible fistula recirculation F2.

A heparin pump is marked by the reference numeral 70 and, as can be seen from FIG. 1, is connected to the arterial branch A and conveys the heparin into this branch.

The elements of the blood circuit shown are controlled by a control or regulation unit, not shown, of the dialysis machine.

Reference symbol CO marks the cardiac output and reference symbol TBV marks the total blood volume of the patient.

In the example shown here, the blood flow $Q_B$ during the treatment is 300 ml/min and the fistula flow is 1 ml/min.

CO is furthermore 5 l/in and TBV is 5 l in the example shown.

The exemplary values and the schematic flows are shown again in FIG. 2.

In accordance with the above-named formula, T=TBV/CO=1 min.

In accordance with the invention, the bolus application time B for the anticoagulant thus has to be set to a value of 1 min or more, preferably to 2 min, i.e. the anticoagulant is added to the extracorporeal circuit by means of the pump 70 over a duration of e.g. 2 min. This addition preferably takes place prior to the start of the dialysis treatment.

The calculation of B takes place in a processing unit of the dialysis machine that accesses a memory in which the values for TBV and CO are stored individually to the patient.

It is also conceivable that the dialysis machine has a reading device that reads in these value from a patient card or the like.

After the addition of the anticoagulant, the blood treatment starts by switching on the blood pump 20 and the dialyzate pump, not shown.

If it is assumed that $V_{hep}$ is the volume of heparin to be added, there results for the flow rate $Q_{hep}$ at which the pump 70 conveys $$Q_{hep} = V_{hep}/B = V_{hep}/2 \text{ min.}$$

This desired conveying speed is indicated to the pump 70 by the control or regulation unit or by said processing unit of the dialysis machine.

The invention claimed is:

1. A method comprising adding an anticoagulant bolus to blood of a patient over a bolus addition time B, wherein the bolus addition time B depends on TBV and CO, with TBV representing total blood volume of the patient and CO representing cardiac output of the patient.

2. The method in accordance with claim 1, wherein the bolus addition time B is equal to or greater than T, where T=TBV/CO.

3. The method in accordance with claim 1, wherein the anticoagulant bolus is added at a volume $V_{hep}$ and a rate $Q_{hep}$, where $Q_{hep} = V_{hep}/B$.

4. The method in accordance with claim 1, wherein the anticoagulant bolus is heparin.

5. The method in accordance with claim 1, wherein addition of the anticoagulant bolus takes place by a pump.

6. The method in accordance with claim 1, wherein addition of the anticoagulant bolus takes place into an extracorporeal circuit of a blood treatment machine.

7. The method in accordance with claim 1, wherein addition of the anticoagulant bolus is carried out prior to a blood treatment of the patient.

8. The method in accordance with claim 1, wherein at least one of TBV and CO is determined or is read out of a memory prior to the anticoagulant bolus addition.

9. The method of claim 6, wherein the blood treatment machine is a dialysis machine.

10. The method of claim 7, wherein the blood treatment is a dialysis treatment.

11. A blood treatment machine comprising:
    at least one apparatus for adding an anticoagulant bolus to the blood of a patient,
    a processing unit that is programmed to determine a bolus addition time B in dependence on TBV and CO, with TBV representing total blood volume of the patient and CO representing cardiac output of the patient,
    a memory is provided in which the values for TBV and/or CO are stored, and
    means for administering the anticoagulant bolus within the bolus addition time B.

12. The blood treatment machine in accordance with claim 11, wherein the bolus addition time B is determined by the processing unit such that B>T is satisfied, where T=TBV/CO.

13. The blood treatment machine in accordance with claim 11, wherein the means for administering the anticoagulant are designed as a pump, with the pump being arranged such that the pump conveys the anticoagulant into an extracorporeal blood circuit of the blood treatment machine.

14. The blood treatment machine in accordance with claim 11, wherein the blood treatment machine is a dialysis machine.

* * * * *